(12) United States Patent
Jansen et al.

(10) Patent No.: US 6,424,159 B1
(45) Date of Patent: Jul. 23, 2002

(54) METHODS AND APPARATUS FOR MONITORING CONTACT SLIPRING DISCONNECTIONS

(75) Inventors: Michael S. Jansen, Wauwatosa; Jonathan R. Schmidt, Wales, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/557,540

(22) Filed: Apr. 25, 2000

(51) Int. Cl.[7] .................... G01R 31/28; G01R 31/00; G01R 31/02
(52) U.S. Cl. .................... 324/528; 324/512; 324/513; 324/515; 324/517; 324/527
(58) Field of Search ................ 324/512, 513, 324/515, 517, 527, 528

(56) References Cited

U.S. PATENT DOCUMENTS

| | | |
|---|---|---|
| 3,917,995 A * | 11/1975 | Clinton .................. 324/517 |
| 5,018,174 A | 5/1991 | Collins |
| 5,140,696 A | 8/1992 | Fox |
| 5,208,581 A | 5/1993 | Collins |
| 5,397,996 A * | 3/1995 | Keezer ................... 324/754 |
| 5,514,966 A * | 5/1996 | Kawamura et al. ......... 324/539 |
| 5,530,424 A | 6/1996 | Harrison et al. |
| 5,577,026 A | 11/1996 | Gordon et al. |
| 6,292,919 B1 | 9/2001 | Fries et al. |
| 6,301,324 B1 | 10/2001 | Pearson, Jr. et al. |

\* cited by examiner

Primary Examiner—N. Le
Assistant Examiner—Wasseem H Hamdan
(74) Attorney, Agent, or Firm—Carl B. Horton, Esq.; Armstrong Teasdale LLP

(57) ABSTRACT

A method and apparatus for detecting interruptions of continuity in a circuit is provided. The method includes transmitting a signal through a brush contacting a conductive band of a slipring, wherein the brush and the slipring have a relative motion. The apparatus is configured to determine a circuit interruption using a plurality of parameters of the signal transmitted through the brush and the slipring, and provide an indication of an interruption when the parameters of the signal transmitted through the brush and slipring are indicative of a circuit interruption.

18 Claims, 2 Drawing Sheets

METHODS AND APPARATUS FOR MONITORING CONTACT SLIPRING DISCONNECTIONS

BACKGROUND OF THE INVENTION

This invention relates generally to methods and apparatus for diagnosing intermittent electrical circuits, and more particularly to methods and apparatus for diagnosing intermittent communications in electrical circuits using brushes and sliprings, including circuits used CT scanning systems using sliprings to send information between stationary and rotating sides of a gantry.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Data and instructions are communicated bidirectionally between electronics on stationary and rotating sides of the gantry. For example, communication is sent across a copper band on a slipring. A brush block maintains an electrical connection to the copper band. A problem with known systems of this type is that there is no indication of whether a connection is broken or whether the connection is simply inactive, with no data being sent. Moreover, sliprings also are known to have problems with "micro disconnects," in which a brush temporarily loses electrical contact from the slipring.

It would therefore be desirable to provide methods and apparatus to monitor the state of brush contacts while a system, such as a CT imaging system, is in operation, and to provide a diagnosis of disconnection events that occur.

BRIEF SUMMARY OF THE INVENTION

There is therefore provided, in one embodiment of the present invention a method for detecting interruptions of continuity in a circuit, including steps of transmitting a signal through a brush contacting a conductive band of a slipring, the brush and slipring having a relative motion; determining whether parameters of the signal transmitted through the brush and the slipring are indicative of a circuit interruption; and providing an indication of an interruption when the parameters of the signal transmitted through the brush and slipring are indicative of a circuit interruption.

This embodiment provides a method for monitoring the state of brush contacts within a system, such as a CT imaging system, while it is in operation. In addition, information provided by this method embodiment can be used to localize and diagnose disconnections when they occur.

DETAILED DESCRIPTION OF THE INVENTION

Figure 1:
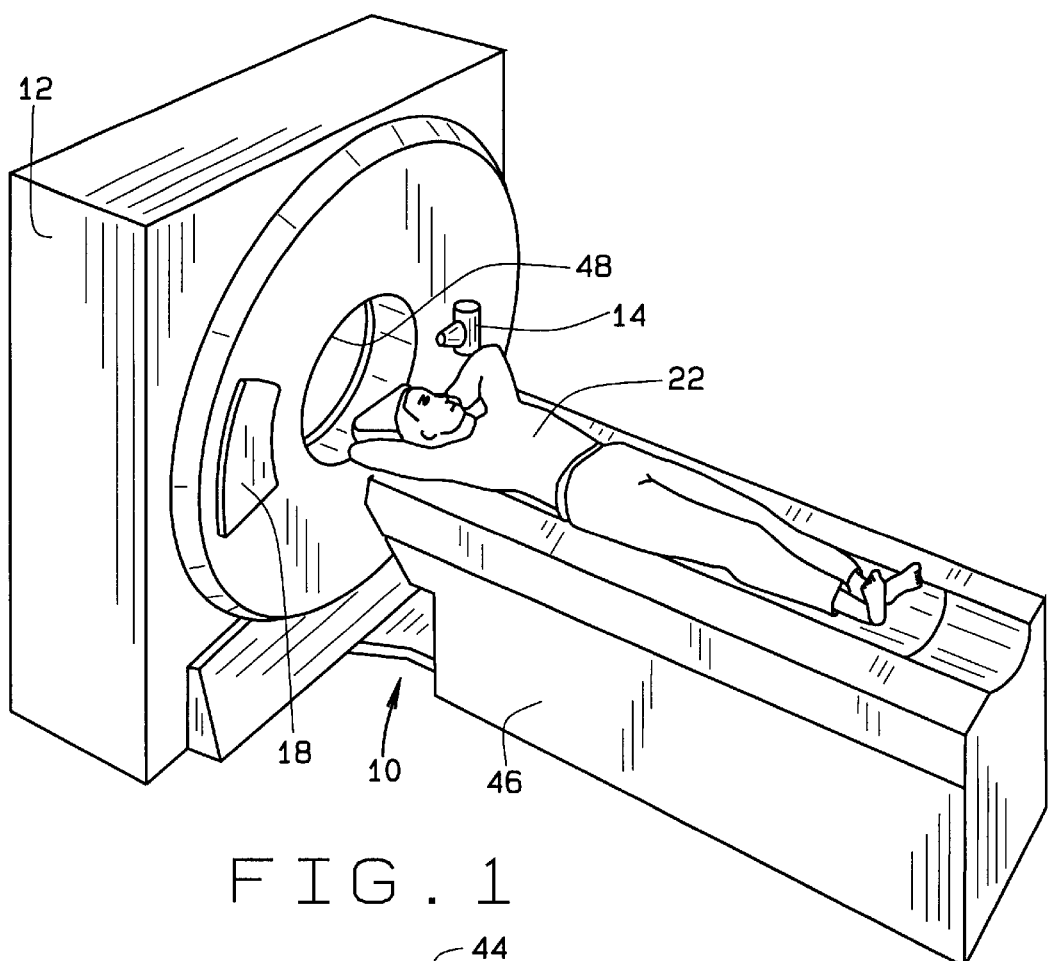
FIG. 1 is a pictorial view of a CT imaging system.
Figure 2:
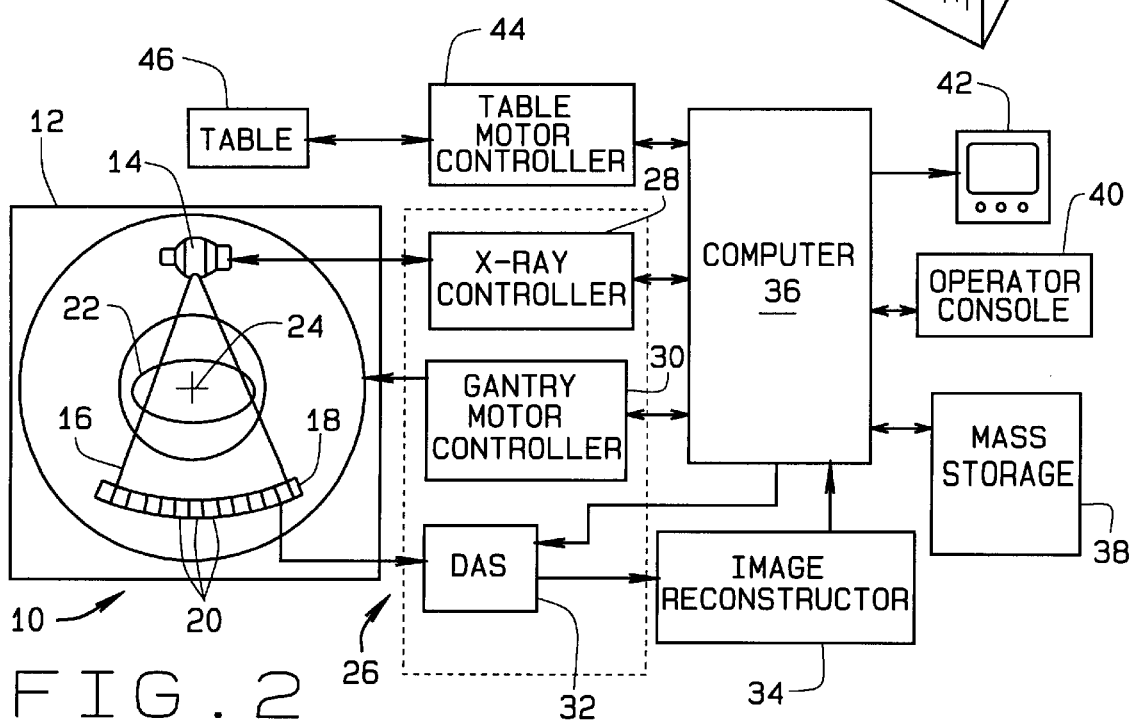
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
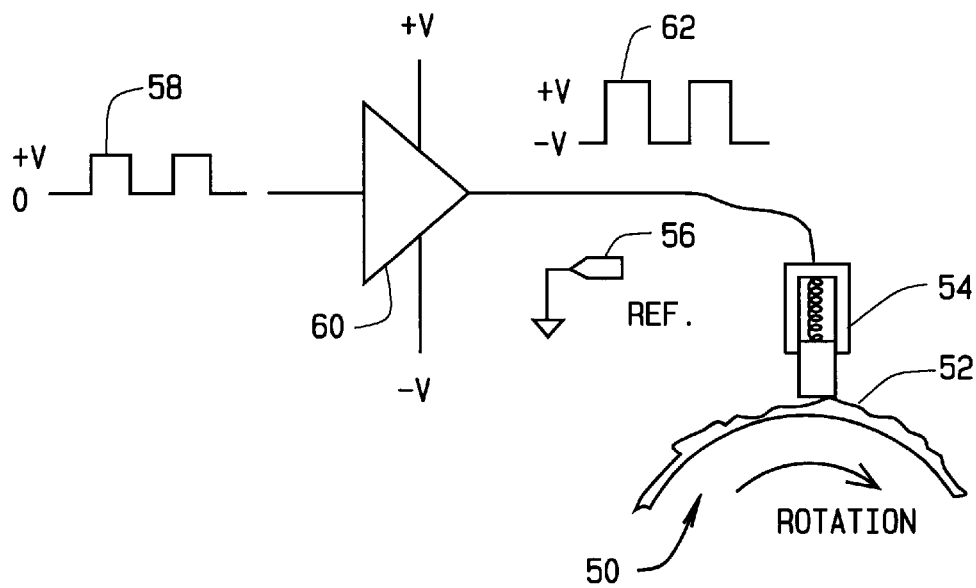
FIG. 3 is a block diagram of a transmitter on one side of the gantry of the CT imaging system of FIGS. 1 and 2, showing transmission of a signal to the other side of the gantry via a brush and a slipring.
Figure 4:
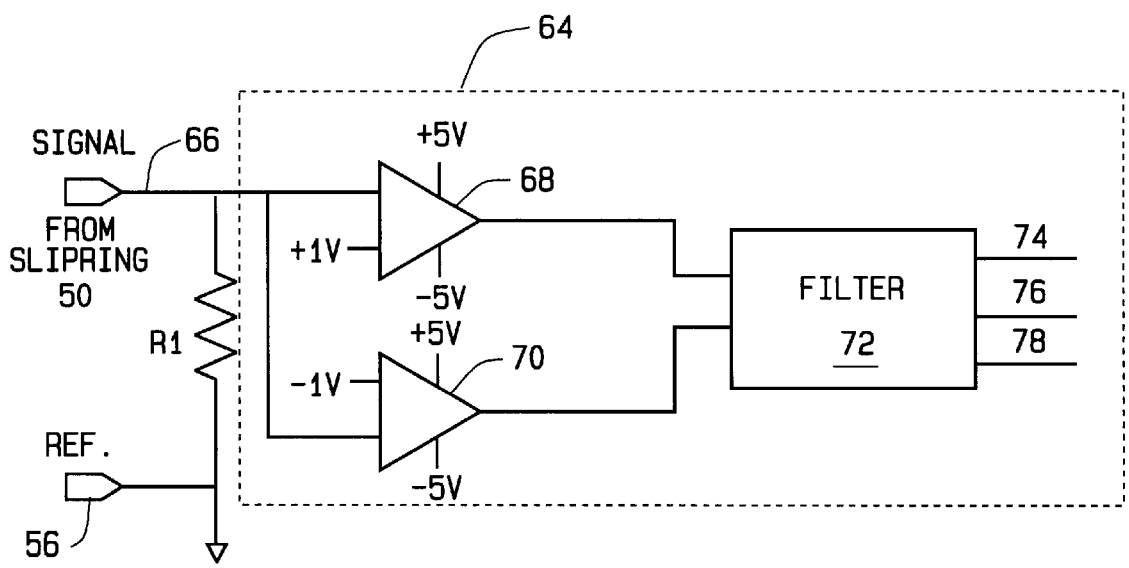
FIG. 4 is a drawing of a portion of a receiver on the other side of the gantry from the transmitter shown in FIG. 3.

Referring to FIGS. 3 and 4, a slipring 50 is used to send information between rotating and stationary sides of gantry 12. Electrical communication is established via a conductive band 52 of slipring 50 in gantry 12. Brush 54 maintains physical and electrical contact with conductive band 52, which is, for example, a copper band. Although only one of each is shown in FIGS. 3 and 4, three conductive bands 52 and three brush blocks 54 are provided in one embodiment, one band 52 and one brush block 54 for transmission in each direction. Another conductive band (not shown in FIGS. 3 and 4) is provided as a reference band having a reference voltage 56.

Because similar circuitry is used for transmission of signals in each direction, only transmission of signals in one direction is shown and described. However, for transmission in both directions, different relative motions of brush 54 and slipring 50 (actually conductive band 52) may be required for different sliprings 50. For convenience, it shall be assumed in this description that slipring 50 is rotating and brush 54 is stationary.

Signals 58 representing serial data are amplified by amplifier 60 into bipolar signals 62 and are received by receiver 64, only an input section of which is shown in FIG. 4. A reference signal 56 is connected to signal line 66 via a resistor R1 (for example, a 1 kilohm resistor). This connection causes a floating condition appears as zero (0) volts with respect to reference 56. During operation, input signals on line 66 transition between +5V and −5V, for example, although other embodiments utilize different ranges. In one embodiment, a finite transition time between +5V and −5V is provided to limit radiation across slipring 50, but the transition time is limited to 50 nanoseconds (ns). The limitation on transition time allows receiver 64 to discriminate between normal transitions and actual circuit disconnections.

In one embodiment, two comparators 68 and 70 are used in receiver 64 as input devices. Comparators 68 and 70 are provided with reference voltages V1 and V2 that define a voltage band around the floating condition voltage that lies strictly within the maximum and minimum voltages of bipolar signal 62. ("Strictly within," as used herein, is intended to mean that the range does not include voltages equal to the maximum and minimum voltages of bipolar signal 62.) For example, in one embodiment, comparator 68 is provided with a +1V reference and comparator 70 is provided with a −1V reference. Outputs of both comparators 68 and 70 are used to determine when line 66 is floating (i.e., in the voltage band between −1V and +1V, or at about 0V, plus or minus a volt of noise). A table showing a relationship of the outputs of comparators 68 and 70 for various operating conditions is given below.

TABLE I

| Output of Comparator 68 | Output of Comparator 70 | State |
| --- | --- | --- |
| 0 | 1 | Good |
| 1 | 0 | Good |
| 0 | 0 | Disconnect |
| 1 | 1 | Failure |

(Note that this embodiment indicates a receiver failure when outputs from both comparators 68 and 70 are high.) Floating disconnects shorter than 50 ns are filtered by filter 72. In one embodiment, floating disconnects indicated by receiver circuit 64 are logged in accordance with their severity. For example, a disconnect longer than 50 ns, but shorter than 200 ns, is logged as having no impact on communications in a system having bit times of 400 ns. Disconnects between 200 ns and 1.6 μs are logged as a disconnect having a minor impact on communication, and disconnects longer than 1.6 μs are logged as being disruptive of communication. In one embodiment, filter 72 has three separate outputs 74, 76, 78 for indicating disconnects of three levels of severity, but other embodiments code severity level in different ways. Filter 72 in conjunction with comparators 68 and 70 provide an indication of a circuit interruption when parameters of bipolar signal 62 transmitted through brush 54 and slipring 50 are indicative of a circuit interruption. In the illustrated embodiment, the parameters are voltage and time, and indication of the interruption occurs when the voltage is within a preselected range (e.g., −1V to +1V) for at least a preselected period of time. Also, filter 72 classifies indicated interruptions according to a length of time a voltage transmitted through the brush and the slipring is within the preselected range of voltage.

In one embodiment, receiver 64 in conjunction with computer 36 generates a log record of disconnects. This log record allows a field service engineer to monitor degradation of a communication link and to take corrective action before significant problems are observed by a user of a CT imaging system 10. For example, a large number of short disconnects may provide an early indication of a brush 54 needing replacement, even though no noticeable effect on communication has been observed. A sufficiently large number of short disconnects may indicate a more serious brush 54 or slipring 50 wear problem. Longer disconnects may indicate a brush 54 problem or a broken or intermittent cable connection. Brush 54 or slipring 50 problems can be directly located by correlating the disconnections with a gantry rotation angle. In one embodiment, computer 36, which also controls rotation of gantry 12, correlates logged disconnects with a rotation angle of gantry 12 and/or slipring 50. Gantry 12 can also be rotated under manual control to locate a disconnect.

It will thus be observed that the embodiments of the present invention described herein can be used for monitoring the state of brush contacts within a system, such as a CT imaging system, while it is in operation. In addition, information provided by embodiments of the present invention can be used to localize and diagnose disconnections when they occur.

Although the invention is described in conjunction with a CT imaging system 10, the invention is also applicable to other types of systems. For example, the invention is applicable to any other system having communication, whether unidirectional or bidirectional, across a slipring, whether or not bipolar modulation is used. In other systems in which a "floating zone" can be defined, the present invention may be modified to detect input signals within that zone to detect disconnects or other degradation problems. In some embodiments, currents rather than voltages are compared to determine when interruptions occur. (The comparison of currents is considered equivalent to the comparison of voltages for purposes of this invention, because of their relationship under Ohm's law.)

While the invention has been described in terms of various specific embodiments, those skilled in the art will recognize that the invention can be practiced with modification within the spirit and scope of the claims.

What is claimed is:

1. A method for detecting interruptions of continuity in a circuit, comprising:

transmitting a signal through a brush contacting a conductive band of a slipring, the brush and slipring having a relative rotational motion;

determining a circuit interruption using a plurality of parameters of the signal transmitted through the brush and the slipring; and providing an indication of an interruption when the parameters of the signal transmitted through the brush and slipring are indicative of a circuit interruption, wherein a first of said parameters is time and a second of said parameters is selected from the group consisting of voltage and current, and said providing an indication of an interruption is conditioned upon the second parameter being strictly within a preselected range for at least a preselected period of time.

2. A method in accordance with claim 1 wherein transmitting a signal through the brush and the slipring comprises the step of transmitting a bipolar signal through the brush and the slipring.

3. A method in accordance with claim 2 wherein the bipolar signal has a minimum and maximum signal voltage range, the second parameter is voltage, and voltages within the preselected range of voltage are within the minimum and maximum signal voltage range.

4. A method in accordance with claim 3 further comprising the step of classifying the indicated interruption in accordance with a length of time the voltage of the signal transmitted through the brush and the slipring is within the preselected range of voltage.

5. A method in accordance with claim 1 wherein providing an indication of an interruption when the parameters of the signal transmitted through the bush and the slipring are indicative of a circuit interruption comprises providing an indication of an angle of rotation of the slipring.

6. A method in accordance with claim 5 wherein a first of said parameters is time and a second of said parameters is selected from the group consisting of voltage and current, and the step of providing an indication of an interruption is conditioned upon the second parameter being strictly within a preselected range for at least a preselected period of time.

7. A method in accordance with claim 6 wherein transmitting a signal through a brush and the slipring comprises the step of transmitting a bipolar signal through the brush and the slipring.

8. A method in accordance with claim 7 wherein the bipolar signal has a minimum and maximum signal voltage range, the second parameter is voltage, and voltages within the preselected range of voltage are within the minimum and maximum signal voltage range.

9. A method in accordance with claim 8 further comprising the step of classifying the indicated interruption in accordance with a length of time the voltage of the signal transmitted through the brush and the slipring is within the preselected range of voltage.

10. An apparatus for reliably transmitting an electrical signal between components moving relative to one another, said apparatus comprising:

a brush contact; and a slipring having a conductive band contacting said brush contact and moving in a relative rotational motion hereto, the electrical signal being communicated between the relatively moving components through said brush contact and said conductive band of said slipring; and said apparatus further being configured to:
determine a circuit interruption using a plurality of parameters of the signal transmitted through the brush and the slipring; and
provide an indication of an interruption when the parameters of the signal transmitted through the brush and slipring are indicative of a circuit interruption, wherein a first of said parameters is time and a second of said parameters is selected from the group consisting of voltage and current, and wherein said apparatus is configured to condition providing said indication of an interruption upon the second parameter being within a preselected range for at least a preselected period of time.

11. An apparatus in accordance with claim 10 wherein said apparatus is configured to transmit a bipolar signal through said brush and said slipring.

12. An apparatus in accordance with claim 11 wherein the bipolar signal has a minimum and maximum signal voltage range, said second parameter is voltage, and voltages within said preselected range of voltage are within said minimum and maximum signal voltage range.

13. An apparatus in accordance with claim 12 further configured to classify indicated interruptions in accordance with a length of time the voltage of the signal transmitted through said brush and said slipring is within said preselected range of voltage.

14. An apparatus for reliably transmitting an electrical signal between components moving relative to one another, said apparatus comprising:

a brush contact; and a slipring having a conductive band contacting said brush contact and moving in a relative rotational motion thereto, the electrical signal being communicated between the relatively moving components through said brush contact and said conductive band of said slipring; and said apparatus further being configured to:

determine a circuit interruption using a plurality of parameters of the signal transmitted through the brush and the slipring; and provide an indication of an interruption when the parameters of the signal transmitted through the brush and slipring are indicative of a circuit interruption, wherein said apparatus being configured to provide an indication of an interruption when the parameters of the signal transmitted though the brush and the slipring are indicative of a circuit interruption comprises said apparatus being configured to provide an indication of an angle of rotation of the slipring.

15. An apparatus in accordance with claim 14 wherein a first of said parameters is time and a second of said parameters is selected from the group consisting of voltage and current, and wherein said apparatus is configured to condition providing said indication of an interruption upon the second parameter being within a preselected range for at least a preselected period of time.

16. An apparatus in accordance with claim 15 wherein said apparatus is configured to transmit a bipolar signal through said brush and said slipring.

17. An apparatus in accordance with claim 16 wherein the bipolar signal has a minimum and maximum signal voltage range, said second parameter is voltage, and voltages within said preselected range of voltage are within said minimum and maximum signal voltage range.

18. An apparatus in accordance with claim 17 further configured to classify indicated interruptions in accordance with a length of time the voltage of the signal transmitted through said brush and said slipring is within said preselected range of voltage.

* * * * *

UNITED STATES PATENT AND TRADEMARK OFFICE
CERTIFICATE OF CORRECTION

PATENT NO. : 6,424,159 B1
DATED : July 23, 2002
INVENTOR(S) : Michael S. Jansen et al.

It is certified that error appears in the above-identified patent and that said Letters Patent is hereby corrected as shown below:

Column 5,
Line 26, delete "bush" insert therefor -- brush --.
Line 55, delete "hereto" insert therefor -- thereto --.

Column 6,
Line 41, delete "transmitted though" insert therefor -- transmitted through --.

Signed and Sealed this

Eleventh Day of November, 2003

JAMES E. ROGAN
*Director of the United States Patent and Trademark Office*